(12) United States Patent
Miller et al.

(10) Patent No.: US 10,272,261 B2
(45) Date of Patent: Apr. 30, 2019

(54) METHODS AND COMPOSITIONS FOR TREATING OCULAR GLAUCOMA

(71) Applicant: Massachusetts Eye and Ear Infirmary, Boston, MA (US)

(72) Inventors: Joan W. Miller, Winchester, MA (US);
Akihisa Matsubara, Nagoya (JP);
Deeba Husain, Lexington, MA (US);
Evangelos S. Gragoudas, Lexington, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 499 days.

(21) Appl. No.: 14/665,575

(22) Filed: Mar. 23, 2015

(65) Prior Publication Data
US 2016/0016000 A1 Jan. 21, 2016

Related U.S. Application Data

(63) Continuation of application No. 11/191,162, filed on Jul. 27, 2005, now abandoned.
(Continued)

(51) Int. Cl.
*A61F 9/008* (2006.01)
*A61N 5/06* (2006.01)
*A61K 41/00* (2006.01)
*A61F 9/007* (2006.01)
*A61N 5/067* (2006.01)

(52) U.S. Cl.
CPC ............ *A61N 5/062* (2013.01); *A61F 9/008* (2013.01); *A61K 41/0057* (2013.01); *A61K 41/0061* (2013.01); *A61K 41/0071* (2013.01); *A61K 41/0076* (2013.01); *A61F 9/0079* (2013.01); *A61F 9/00781* (2013.01);
(Continued)

(58) Field of Classification Search
CPC ................................. A61F 9/008; A61N 5/06
USPC ....................................... 606/4–6; 607/88–89
See application file for complete search history.

(56) References Cited

U.S. PATENT DOCUMENTS 5,171,749 A  12/1992  Levy et al.
5,214,036 A   5/1993  Allison et al.
(Continued)

FOREIGN PATENT DOCUMENTS

WO  WO-98/025648  6/1998
WO  WO-00/051638  9/2000
(Continued)

OTHER PUBLICATIONS

Tsilimbaris et al. "Ciliary body PDT in pigmented rabbit eyes: Effect of single and repeated treatment", 2000, Current Eye Research, vol. 20, No. 6, pp. 469-479 (abstract only).*
(Continued)

*Primary Examiner* — Lynsey C Eiseman
(74) *Attorney, Agent, or Firm* — Goodwin Procter LLP

(57) ABSTRACT

The invention provides a photodynamic therapy-based method for treating ocular glaucoma. A photosensitizer, for example, a benzoporphyrin derivative photosensitizer, is administered to a mammal either having or at risk of developing ocular glaucoma. The photosensitizer, when present in the ciliary body, is activated by light, for example, light from a laser. The treatment results in a reduction of intraocular pressure within the treated eye, which can persist for a prolonged period of time.

25 Claims, 2 Drawing Sheets
Specification includes a Sequence Listing.

Related U.S. Application Data

(60) Provisional application No. 60/593,037, filed on Jul. 30, 2004.

(52) U.S. Cl.
 CPC ............... *A61F 2009/00868* (2013.01); *A61F 2009/00891* (2013.01); *A61N 2005/067* (2013.01); *A61N 2005/0662* (2013.01)

(56) References Cited

U.S. PATENT DOCUMENTS

| | | | |
|---|---|---|---|
| 5,283,255 A | | 2/1994 | Levy et al. |
| 5,478,338 A | * | 12/1995 | Reynard ............. A61F 9/00745 606/15 |
| 5,707,986 A | * | 1/1998 | Miller .................. A61K 9/0019 514/185 |
| 5,773,609 A | | 6/1998 | Robinson et al. |
| 5,798,349 A | | 8/1998 | Levy et al. |
| 6,225,303 B1 | | 5/2001 | Miller et al. |
| 6,270,749 B1 | | 8/2001 | Blumenkranz et al. |
| 6,274,614 B1 | | 8/2001 | Richter et al. |
| 6,375,930 B2 | | 4/2002 | Young et al. |
| 2002/0103180 A1 | | 8/2002 | Richter et al. |
| 2006/0021623 A1 | | 2/2006 | Miller et al. |
| 2010/0076419 A1 | | 3/2010 | Chew et al. |

FOREIGN PATENT DOCUMENTS

| | | |
|---|---|---|
| WO | WO-01/074389 | 10/2001 |
| WO | WO-03/028628 | 4/2003 |
| WO | WO-06/015016 | 2/2006 |

OTHER PUBLICATIONS

Ahmed et al. (2003) "Non-Invasive Tonometry in the Mouse," Invest. Ophthalmol. Vis. Sci. 44, E-Abstract 3336-B39 (corresponding abstract first available Feb. 17, 2003, at ARVO website, www.arvo.org).
Arons (2001) "Aging Population Spurs Glaucoma and AMD Research," OptiStock/Vision Care Industry Overview, at http://www.optistock.com/lis01_amd_glaucoma.htm (last visited Jul. 23, 2004) (12 pages).
Bakalash et al. (2002) "Resistance of Retinal Ganglion Cells to an Increase in Intraocular Pressure Is Immune-Dependent," Invest. Ophthalmol. Vis. Sci. 43: 2648-53.
Beckman et al. (1984) "Transceral Ruby Laser Cyclocaogulation," Am. J. Ophthalmol. 98: 788-95.
Benozzi et al. (2002) "Effect of Hyaluronic Acid on Intraocular Pressure in Rats," Invest. Ophthalmol. Vis. Sci. 43(7): 2196-2200.
Bietti (1950) "Surgical Intervention on the Ciliary Body: New trends for the relieft of glaucoma," JAMA 142: 889-97.
Congdon et al. (2004) "Causes and Prevalence of Visual Impairment Among Adults in the United States," Arch. Ophthalmol. 124: 477-85.
Congdon et al. (2004), "Prevalence of Cataract and Pseudophakia/Aphakia Among Adults in the United States," Arch. Ophthalmol. 124: 487-94.
Corneal Thickness and Glaucoma (2003) AgingEye Times web site, available at www.agingeye.net/mainnews/glaucomapachymetry.php (last visited Jul. 30, 2004, as retrieved on Jul. 20, 2004) (3 pages).
Ergun et al. (2004) "Photodynamic Therapy with Verteporfin in Subfoveal Choroidal Neovascularization Secondary to Central Serous Chorioretinopathy," Arch. Ophthalmol. 122(1): 37-41 (abstract only; 2 pages).
Gurwood et al. (Feb. 27, 2004) "Neovascular glaucoma secondary to ischaemic central retinal vein occulsion," Focus On Glaucoma pp. 32-34.
Haddad (1981) "Cyclokryokoagulation," Wien. Klin. Wochenschr. Suppl. 126: 3-18 (Summary in English appears on first page).
Hafezi-Moghadam (Sep. 25-28, 2003) "Photodynamic Therapy of Ciliary Body in Experimental Glaucoma," Abstract (1 page) and Sep. 28, 2003 program (3 pages) for Jahrestagung der DOG, 25.-28.9 2003—Allgemeine Informationen Programme, available at www.dog.org/2003/abstracts/165_e.html (last visited Jul. 23, 2004).
Hagimura et al. (2002) "Persistent Foveal Retinal Detachment After Successful Rhegmatogenous Retinal Detachment Surgery," Amer. J. Ophthalmol. 133 (4): 516-20.
Hill et al. (1995) "Photodynamic Laser Cyclodestruction With Chloroaluminum Sulfonated Phthalocyanine (CASPc) or Photofrin (PII) Vs. Nd:YAG Laser Cyclodestruction in a Pigmented Rabbit Model," Lasers in Surgery and Medicine 17:166-71.
Hill et al. (1996) "Photodynamic Therapy (PDT) of the Ciliary Body With Silicon Naphthalocyanine (SINc) in Rabbits," Lasers in Surgery and Medicine 18: 86-91.
Hill et al. (Nov. 1997) "Photodynamic Therapy of the Ciliary Body With Tin Ethyl Etiopurpurin and Tin Octaethyl Benzochlorin in Pigmented Rabbits," Ophthalmic Surgery and Lasers (11): 948-53.
Hoffmann et al. (Mar. 23, 2004) "Intraocular pressure and ocular pulse amplitude using dynamic contour tonometry and contact lens tonometry," BMC Ophthalmology 4:4, available at http://www.biomedcentral.com/1471-2415/4/4 (last visited Dec. 29, 2008) (7 pages).
Huang et al. (2004) "Comparative Study of the Phototoxicity of Two Chrolin Type Photosensitizers, ATX-S10(Na) and Verteporfin, on Vascular Endothelial and Retinal Pigment Epithelial Cells," Lasers in Surgery and Medicine 34: 216-26.
Husain et al. (Aug. 1997) "Photodynamic therapy and digital angiography of experimental iris neovascularization using liposomal benzoporphyrin derivative," Ophthalmology 104(8): 1242-50.
International Search Report for Application No. PCT/US2005/026587, published Feb. 1, 2007 (6 pages).
Ji et al. (2005) "Effects of Elevated Intraocular Pressure on Mouse Retinal Ganglion Cells," Vision Research 45: 169-79.
Kaiden et al. (1979) "Choroidal Detachment with Flat Anterior Chamber After Cyclocryotherapy," Ann. Ophthalmol. 11: 1111-13 (and 2 journal cover pages).
Matsubara et al. (2004) "Investigating the Effect of Ciliary Body Photodynamic Therapy in Mice," ARVO 2004 Annual Meeting Poster Presentation, Apr. 25, 2004.
Matsubara et al. (2004) "Investigating the Effect of Ciliary Body Photodynamic Therapy in Mice," Invest. Ophthalmol. Vis. Sci. 45, E-Abstract 990-B963 (corresponding abstract first available Feb. 23, 2004, at ARVO website, www.arvo.org).
Matsubara et al. (2005) "Investigating the Effect of Ciliary Body Photodynamic Therapy in a Glaucoma Mouse Model," Invest. Ophthalmol. Vis. Sci. 46, E-abstract 110-B84 (corresponding abstract first available Feb. 22, 2005, at ARVO website, www.arvo.org).
Matsubara et al. (2006) "Investigating the Effect of Ciliary Body Photodynamic Therapy in a Glaucoma Mouse Model," Invest. Ophthalmol. Vis. Sci. 47(6): 2498-2507.
Meads et al. (2004) "Photodynamic therapy with verteporfin is effective, but how big is its effect? Results of a systematic review," Br. J. Ophthalmol. 88(2): 212-17.
Muller et al. (2003) "Treatment of Rubeosis iridis with Photodynamic Therapy with Verteporfin—A New Therapeutic and Prophylactic Option for Patients with the Risk of Neovascular Glaucoma?" Ophthalmic Res. 35: 60-64.
Parodi et al. (Jul. 1, 2004) "Photodynamic Therapy With Verteporfin for Anterior Segment Neovascularizations in Neovascular Glaucoma," Amer. Journal of Ophthalmol. 138 (1):157-58.
Rivellese et al. (2000) "Photodynamic Therapy of Eye Diseases," J. Ophthalmic Nurs. Technol. 19(3): 134-41.
Rizq et al.(2001) "Intraocular pressure measurement at the choroids surface: a feasibility study with implications for implantable Microsystems," Br. J. Ophthalmol. 85: 868-71.
Rodriguez et al. (2002) "Causes of Blindness and Visual Impairment in a Population—based sample of U.S. Hispanics," Ophthalmol. 109: 737-43.
Ryan et al. (Date Unknown) "Photodynamic Therapy (PDT) of the Ciliary Body: A Possible New Cyclodestructive Technique," p. 137 (1 page) supported by ONR N00014-91-C-0134;DOE-FG03 91, ER 61227, NIH CA 46281.

(56) References Cited

OTHER PUBLICATIONS

Schuman (2000) "Cycloablation," Principles and Practice of Ophthalmology Chapter 230, pp. 3013-3023, Albert and Jakobiec (eds.), W.B. Sounders, Phila, PA.

Smith et al. (1969) "Ocular Hazards of Transceral Laser Radiation," Am. J. Ophthalmol. 67:100-10.

Stasi et al. (2003) "Photodynamic Treatment in a Rabbit Model of Glaucoma Surgery," Invest. Ophthalmol. Vis. Sci. 44, E-Abstract 1195-B91 (corresponding abstract first available Feb. 17, 2003, at ARVO website, www.arvo.org).

Treatment of Age-related Macular Degeneration with Photodynamic Therapy (TAP) Study Group (1999) "Photodynamic Therapy of Subfoveal Choroidal Neovascularization in Age-related Macular Degeneration With Verteporfin, One Year Results of 2 Randomized Clinical Trials—TAP Report 1," Archives of Ophthalmology 117: 1329-45.

Tsilimbaris et al. (1997) "Transcleral Ciliary Body Photodynamic Therapy Using Phthalocyanine and a Diode Laser: Functional and Morphologic Implications in Albino Rabbits," Ophthalmic Surgery and Lasers 28(6): 483-94.

Tsilimbaris et al. (2000) "Ciliary body PDT in pigmented rabbit eyes: Effect of single and repeated treatment," Current Eye Research, 20: 469-79.

Tsilimbaris et al. (2003) "Ciliary Body PDT in Pigmented Rabbits using Visudyne and 690 nm Diode Laser," Invest. Ophthalmol. Vis. Sci. 44, E-Abstract 1185-B81 (corresponding abstract first available Feb. 17, 2003, at ARVO website, www.arvo.org).

Wachtlin et al. (2003) "Long-term results after photodynamic therapy with verteporfin for choroidal neovascularizations secondary to inflammatory chorioretinal diseases," Graefes Arch. Clin. Exp. Ophthalmol. 241: 899-906.

Weekers et al. (1961) "Effects of Photocoagulation of Ciliary Body Upon Ocular Tension," Am. J. Ophthalmol. 52: 156-63.

Wolfensberger (2002) "Foveal Reattachment Following Macula-Off Retinal Detachment Occurs Faster After Vitrectomy Than After Buckle Surgery," Abstract for presentation at Club Jules Gonin XXIIIrd Meeting, Sep. 2002, Montreux, Switzerland (1 page).

\* cited by examiner

METHODS AND COMPOSITIONS FOR TREATING OCULAR GLAUCOMA

CROSS-REFERENCE TO RELATED APPLICATION

The present application is a continuation of U.S. application Ser. No. 11/191,162, filed Jul. 27, 2005, which claims priority to and the benefit of U.S. Ser. No. 60/593,037, filed Jul. 30, 2004, the entire disclosures of each of which are incorporated herein by reference for all purposes.

FIELD OF THE INVENTION

The invention relates generally to methods and compositions for treating ocular glaucoma, and more particularly, the invention relates to a photodynamic therapy-based method and associated compositions for treating ocular glaucoma.

BACKGROUND

Glaucoma is the most common cause of blindness and the second leading cause of irreversible blindness among black Americans in the United States (Congdon et al. (2004) ARCH. OPHTHALMOL. 122: 477-85). Glaucoma is also the leading cause of blindness among U.S. Hispanics (Congdon et al. (2004) supra, Rodriguez et al. (2002) OPHTHALMOL. 109:737-43). Glaucoma is a progressive optic neuropathy, which can induce blindness without any warning and often without symptoms.

Glaucoma is characterized by a buildup of fluid within the eye, often causing an increase in intraocular pressure (IOP). The pressure increase damages the optic nerve, resulting in cellular death and vision loss. In a healthy eye, the fluid that contains nutrients and that bathes the eye is continuously drained and replenished. However, in a person with glaucoma, this fluid either does not drain properly or is created in excess, resulting in an increase in intraocular pressure. The elevated intraocular pressure, if left untreated, eventually damages the optic nerve.

As a result, lowering intraocular pressure using medical or surgical therapy is the main therapeutic approach to control and treat this common condition. The currently available treatments, however, have their own problems. Most medications have side effects, lose their efficacy, and require patients' life time compliance. Surgical methods have a high complication risk. Ciliary body destruction by cryotherapy or laser irradiation represents a useful alternative for the management of glaucoma resistant to other modes of therapy (Bietti (1950) JAMA, 142:889-897, Wekers et al. (1961) AM. J. OPHTHALMOL. 52:156-63, Smith et al. (1969) AM. J. OPHTHALMOL. 67:100-10). However, the current cyclodestructive techniques have a high rate of side-effects including loss of vision, hypotony, macular edema or phthisis bulbi (Beckman et al. (1984) AM. J. OPHTHALMOL. 98:788-95, Haddad (1981) WIEN. KLIN. WOCHENSCHR. SUPPL. 126:1-18, Kaiden et al. (1979) ANN. OPHTHALMOL. 11:1111-3).

Accordingly, there is still an ongoing need for new methods for treating glaucoma, which can reduce intraocular pressure for extended periods of time, but without the side effects of other currently available treatments.

SUMMARY

The invention is based, in part, upon the discovery that it is possible to perform photodynamic therapy (PDT) on the ciliary body of the eye so as to reduce intraocular pressure within the eye for a prolonged period of time. The invention is also based, in part, upon the discovery that is possible to perform PDT on the ciliary body of the eye, particularly in those patients at risk of developing or having glaucoma, in a manner that preserves the viability of retinal ganglion cells.

In one aspect, the invention provides a method of reducing the intraocular pressure in a mammalian eye having a ciliary body. The method includes the steps of: (a) administering to a mammal, an amount of photosensitizer sufficient to accumulate within the ciliary body; and (b) irradiating a region within the ciliary body with light so as to activate the photosensitizer. The activated photosensitizer then causes a reduction in the intraocular pressure of the eye relative to the intraocular pressure in the eye prior to irradiation. This reduction in intraocular pressure can persist for a prolonged period of time, for example, at least 4 weeks, at least 5 weeks, at least 6 weeks, at least 7 weeks, or at least 8 weeks.

A variety of photosensitizers can be used in the practice of the invention. In one embodiment, the photosensitizer is a benzoporphyrin derivative, for example, benzoporphyrin derivative mono-acid. Practice of the invention can reduce the intraocular pressure in the eye by at least 20%, at least 30%, or at least 40% of the intraocular pressure in the eye prior to irradiation. Furthermore, the method can reduce the intraocular pressure by at least 20% for at least 4 weeks, at least 5 weeks, at least 6 weeks, at least 7 weeks, or at least 8 weeks.

In another aspect, the invention provides a method of treating glaucoma in a mammalian eye having a ciliary body. The method includes the steps of: (a) administering to a mammal, an amount of photosensitizer, for example, a benzoporphyrin derivative photosensitizer, for example, a benzoporphyrin derivative mono acid photosensitizer, sufficient to accumulate in the ciliary body; and (b) irradiating a region within the ciliary body with light so as to activate the photosensitizer. The photosensitizer, once activated, causes a reduction in the intraocular pressure of the eye relative to the intraocular pressure in the eye prior to irradiation. This reduction in intraocular pressure can persist for a prolonged period of time, for example, at least 4 weeks, at least 5 weeks, at least 6 weeks, at least 7 weeks, or at least 8 weeks.

During the method, the irradiation reduces the intraocular pressure in the eye by at least 20%, by at least 30%, or by at least 40% of the intraocular pressure in the eye prior to irradiation. Furthermore, the method reduces the intraocular pressure for at least 4 weeks, at least 5 weeks, at least 6 weeks, at least 7 weeks, or at least 8 weeks. In some embodiments, the method reduces the intraocular pressure by at least 20% for at least 4 weeks, at least 5 weeks, at least 6 weeks, at least 7 weeks, or at least 8 weeks.

In another aspect, the invention features a method of reducing intraocular pressure for a prolonged period of time in an eye having a ciliary body. The method includes the steps of administering to a mammal an amount of a benzoporphyrin derivative photosensitizer sufficient to accumulate in the ciliary body, and irradiating a region of the ciliary body with light, wherein the light activates the photosensitizer and wherein the activated photosensitizer causes a reduction in the intraocular pressure in the eye relative to the intraocular pressure in the eye prior to irradiation for a prolonged period of time.

In another aspect, the invention includes a method of preserving retinal ganglion cell viability in a mammalian eye having a ciliary body and at risk of developing or having glaucoma. The method includes the steps of administering to a mammal an amount of photosensitizer, for example, a benzoporphyrin derivative photosensitizer, for example, a benzoporphyrin derivative mono acid photosensitizer, sufficient to accumulate in the ciliary body, and irradiating a region of the ciliary body so as to activate the photosensitizer, such that retinal ganglion cell viability is preserved. The activated photosensitizer can cause a decrease in the intraocular pressure in the eye relative to the intraocular pressure in the eye prior to irradiation. This decrease in intraocular pressure can be for a prolonged period of time, for example, at least 4 weeks, at least 5 weeks, at least 6 weeks, at least 7 weeks, or at least 8 weeks. The irradiation can reduce the intraocular pressure in the eye by at least 20%, by at least 30%, or by at least 40% of the intraocular pressure in the eye prior to irradiation. Furthermore, the intraocular pressure can be reduced, for example, by at least 20%, for at least 4 weeks, at least 5 weeks, at least 6 weeks, at least 7 weeks, or at least 8 weeks.

Any of the preceding aspects of the invention can have any one or a combination of the following features. The amount of photosensitizer can be about 1 mg/kg. The light can have a wavelength of about 689 nm. The irradiating step can include a fluence of about 100 Joules/cm$^2$. The irradiating step can include an irradiance of about 1800 mW/cm$^2$. The irradiating step can include irradiation covering 180 degrees of the ciliary body. The reduction of intraocular pressure can be continuous over the prolonged period of time.

The foregoing aspects and embodiments of the invention may be more fully understood by reference to the following figures, detailed description and claims.

BRIEF DESCRIPTION OF THE DRAWINGS

The objects and features of the invention may be more fully understood by reference to the drawings described below in which.

DETAILED DESCRIPTION

Figure 1:
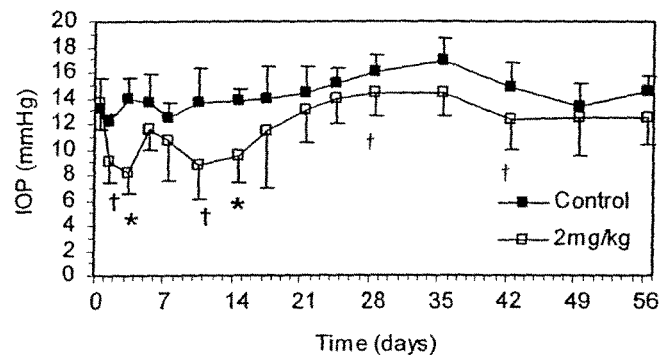
FIG. 1 is a graph showing the mean changes in intraocular pressure after PDT treatment of normal mice with 2.0 mg/kg verteporfin (open boxes) or without PDT treatment in a control eye (filled boxes). Values are mean±SD. *P<0.01 compared with controls. †P<0.05 compared with controls.

The invention relates to a photodynamic therapy-based method for reducing intraocular pressure in a mammalian eye, for example, a human eye, for an extended or prolonged period of time. The method is particularly useful in treating or controlling glaucoma in an individual. Additionally, the invention relates to a PDT method, particularly in those patients at risk of having or developing glaucoma, that preserves the viability of retinal ganglion cells.

The method requires administering a photosensitizer to a mammal in need of such treatment in an amount sufficient to permit an effective amount (i.e., an amount sufficient to facilitate PDT) of the photosensitizer to localize in the ciliary body of the eye. After administration of the photosensitizer, one or more regions of the ciliary body are irradiated with light, for example, laser light, under conditions that allow that the light to be absorbed by the photosensitizer. The photosensitizer, when activated by the light, generates singlet oxygen and free radicals, for example, reactive oxygen species, that damage the surrounding tissue within the treated portions of the ciliary body.

The treatment reduces the intraocular pressure by at least 20%, at least 30%, or at least 40% of the intraocular pressure prior to treatment. Furthermore, the treatment causes a reduction in the intraocular pressure for a prolonged period of time, i.e., at least four weeks. In some embodiments, the reduction in intraocular pressure persists, for example, for at least 4 weeks, for at least 5 weeks, for at least 6 weeks, for at least 7 weeks, for at least 8 weeks, for at least 3 months, or for at least 6 months. The reduction of intraocular pressure can be continuous over the prolonged period of time.

It is contemplated that a variety of photosensitizers useful in PDT may be useful in the practice of the invention and include, for example, amino acid derivatives, azo dyes, xanthene derivatives, chlorins, tetrapyrrole derivatives, phthalocyanines, and assorted other photosensitizers.

Amino acid derivatives include, for example, 5-aminolevulinic acid (Berg et al. (1997) PHOTOCHEM. PHOTOBIOL 65: 403-409; El-Far et al. (1985) CELL. BIOCHEM. FUNCTION 3, 115-119). Azo dyes, include, for example, Sudan I, Sudan II, Sudan III, Sudan IV, Sudan Black, Disperse Orange, Disperse Red, Oil Red O, Trypan Blue, Congo Red, β-carotene (Mosky et al. (1984) EXP. RES. 155, 389-396). Xanthene derivatives, include, for example, rose bengal.

Chlorins include, for example, lysyl chlorin p6 (Berg et al. (1997) supra) and etiobenzochlorin (Berg et al. (1997) supra), 5, 10, 15, 20-tetra (m-hydroxyphenyl) chlorin (M-THPC), N-aspartyl chlorin e6 (Dougherty et al. (1998) J. NATL. CANCER INST. 90: 889-905), and bacteriochlorin (Korbelik et al. (1992) J. PHOTOCHEM. PHOTOBIOL. 12: 107-119).

Tetrapyrrole derivatives include, for example, lutetium texaphrin (Lu-Tex, PCI-0123) (Dougherty et al. (1998) supra, Young et al. (1996) PHOTOCHEM. PHOTOBIOL. 63: 892-897); benzoporphyrin derivative (BPD) (U.S. Pat. Nos. 5,171,749, 5,214,036, 5,283,255, and 5,798,349, Joni et al. (1990) LASERS MED. SCI. 5, 115-120), benzoporphyrin derivative mono acid (BPD-MA) (U.S. Pat. Nos. 5,171,749, 5,214, 036, 5,283,255, and 5,798,349, Berg et al. (1997) supra, Dougherty et al. (1998) supra), hematoporphyrin (Hp) (Joni et al. (1990) supra), hematoporphyrin derivatives (HpD) (Berg et al. (1997) supra, West et al. (1990) IN. J. RADIAT. BIOL. 58: 145-156), porfimer sodium or Photofrin (PHP) (Berg et al. (1997) supra), Photofrin II (PII) (He et al. (1994) PHOTOCHEM. PHOTOBIOL. 59: 468-473), protoporphyrin IX (PpIX) (Dougherty et al. (1998) supra, He et al. (1994) supra), meso-tetra(4-carboxyphenyl) porphine (TCPP) (Musser et al. (1982) RES. COMMUN. CHEM. PATHOL. PHARMACOL. 2, 251-259), meso-tetra (4-sulfonatophenyl) porphine (TSPP) (Musser et al. (1982) supra), uroporphyrin I (UROP-I) (El-Far et al. (1985) CELL. BIOCHEM. FUNCTION 3, 115-119), uroporphyrin III (UROP-III) (El-Far et al. (1985) supra), tin ethyl etiopurpurin (SnET2), (Dougherty et al. (1998) supra 90: 889-905) and 13, 17-bis[1-carboxypropionyl]carbamoylethyl-8-etheny-2-hydroxy-3-hydroxyiminoethyliden e-2,7, 12,18-tetranethyl 6 porphyrin sodium (ATX-S10(Na)) Mori et al. (2000) JPN. J. CANCER RES. 91:753-759, Obana et al. (2000) ARCH. OPHTHALMOL. 118:650-658, Obana et al. (1999) LASERS SURG. MED. 24:209-222).

Phthalocyanines include, for example, chloroaluminum phthalocyanine (AlPcCl) (Rerko et al. (1992) PHOTOCHEM. PHOTOBIOL. 55, 75-80), aluminum phthalocyanine with 2-4 sulfonate groups ($AlPcS_{2-4}$) (Berg et al. (1997) supra, Glassberg et al. (1991) LASERS SURG. MED. 11, 432-439), chloro-aluminum sulfonated phthalocyanine (CASPc) (Roberts et al. (1991) J. NATL. CANCER INST. 83, 18-32), phthalocyanine (PC) (Joni et al. (1990) supra), silicon phthalocyanine (Pc4) (He et al. (1998) PHOTOCHEM. PHOTOBIOL. 67: 720-728, Jori et al. (1990) supra), magnesium phthalocyanine ($Mg^{2+}$-PC) (Jori et al. (1990) supra), zinc phthalocyanine (ZnPC) (Berg et al. (1997) supra). Other photosensitizers include, for example, thionin, toluidine blue, neutral red and azure c.

However, preferred photosensitizers include benzoporphyrin and benzoporphyrin derivatives, for example, BPD-MA and BPD-DA, available from QLT, Inc., Vancouver, Canada. Liposomal formulations of BPD-MA are available, for example, from Novartis Ophthalmics, Inc., Duluth, Ga.

The photosensitizer preferably optionally is formulated into a delivery system that delivers high concentrations of the photosensitizer to the ciliary body. Such formulations may include, for example, the combination of a photosensitizer with a carrier that delivers higher concentrations of the photosensitizer to the ciliary body and/or coupling the photosensitizer to a specific binding ligand that binds preferentially to a specific cell surface component of the ciliary body.

In certain embodiments, the photosensitizer can be combined with a lipid based carrier. For example, liposomal formulations have been found to be particularly effective at delivering the photosensitizer, green porphyrin, and more particularly BPD-MA to the low-density lipoprotein component of plasma, which in turn acts as a carrier for the photosensitizer. Certain photosensitizers, for example, green porphyrins, and in particular BPD-MA, interact strongly with lipoproteins. LDL itself can be used as a carrier, but LDL is considerably more expensive and less practical than a liposomal formulation. LDL, or preferably liposomes, are thus preferred carriers for the green porphyrins since green porphyrins strongly interact with lipoproteins and are easily packaged in liposomes. Compositions of green porphyrins formulated as lipocomplexes, including liposomes, are described, for example, in U.S. Pat. Nos. 5,214,036, 5,707, 608 and 5,798,349. Liposomal formulations of green porphyrin can be obtained from QLT, Inc., Vancouver, Canada. It is contemplated that certain other photosensitizers may likewise be formulated with lipid carriers, for example, liposomes or LDL, to deliver the photosensitizer to the ciliary body.

Once formulated, the photosensitizer may be administered in any of a wide variety of ways, for example, orally, parenterally, or rectally. Parenteral administration, such as intravenous, transscleral, intramuscular, or subcutaneous, is preferred. Intravenous injection is preferred. The dose of photosensitizer can vary widely depending on the tissue to be treated, the physical delivery system in which it is carried, such as in the form of liposomes, or whether it is coupled to a target-specific ligand, such as an antibody or an immunologically active fragment.

It should be noted that the various parameters used for effective, selective photodynamic therapy in the invention are interrelated. Therefore, the dose should also be adjusted with respect to other parameters, for example, fluence, irradiance, duration of the light used in PDT, and time interval between administration of the dose and the therapeutic irradiation. All of these parameters should be adjusted to modify the ciliary body without significant damage to the surrounding tissue. Without wishing to be bound to theory, the modification may result in a decrease in the production of humor.

Typically, the dose of photosensitizer used is within the range of from about 0.1 to about 20 mg/kg, preferably from about 0.15 to about 5.0 mg/kg, and even more preferably from about 0.25 to about 2.0 mg/kg. Furthermore, in certain circumstances as the dosage of photosensitizer is reduced, for example, from about 2 mg/kg to about 1 mg/kg in the case of green porphyrin or BPD-MA, the fluence required to impart a reduction on the intraocular pressure may increase, for example, from about 50 to about 100 Joules/$cm^2$. Similar trends may be observed with the other photosensitizers discussed herein.

After the photosensitizer has been administered, the ciliary body is irradiated at a wavelength typically around the maximum absorbance of the photosensitizer, usually in the range from about 550 nm to about 750 nm. A wavelength in this range is especially preferred for enhanced penetration into bodily tissues. Preferred wavelengths used for certain photosensitizers include, for example, about 690 nm for benzoporphyrin derivative mono acid, about 630 nm for hematoporphyrin derivative, about 675 nm for chloro-aluminum sulfonated phthalocyanine, about 660 nm for tin ethyl etiopurpurin, about 730 nm for lutetium texaphyrin, about 670 nm for ATX-S10(NA), about 665 nm for N-aspartyl chlorin e6, and about 650 nm for 5, 10, 15, 20-tetra (m-hydroxyphenyl) chlorin.

As a result of being irradiated, the photosensitizer in its triplet state is thought to interact with oxygen and other compounds to form reactive intermediates, such as singlet oxygen and reactive oxygen species, which can disrupt cellular structures. Possible cellular targets include the cell membrane, mitochondria, lysosomal membranes, and the nucleus. Evidence from tumor and neovascular models suggests that occlusion of the vasculature is a major mechanism of photodynamic therapy, which occurs by damage to the endothelial cells, with subsequent platelet adhesion, degranulation, and thrombus formation.

The fluence during the irradiating treatment can vary widely, depending on the type of photosensitizer used, the type of tissue, the depth of target tissue, and the amount of overlying fluid or blood. Fluences preferably vary from about 10 to about 400 Joules/$cm^2$ and more preferably vary from about 50 to about 200 Joules/$cm^2$. The irradiance varies typically from about 50 mW/$cm^2$ to about 1800 mW/$cm^2$, from about 100 mW/$cm^2$ to about 900 mW/$cm^2$, or from about 150 mW/$cm^2$ to about 600 mW/$cm^2$. It is contemplated that for many practical applications, the irradiance will be within the range of about 300 mW/$cm^2$ to about 900 mW/$cm^2$. However, the use of higher irradiances may be selected as effective and having the advantage of shortening treatment times. For example, an irradiance of 1800 mW/$cm^2$ can be used.

The time of light irradiation after administration of the photosensitizer may be important as one way of maximizing the selectivity of the treatment, thus minimizing damage to structures other than the target tissues. The optimum time following photosensitizer administration until light treatment can vary widely depending on the mode of administration, the form of administration such as in the form of liposomes or as a complex with LDL, and the type of target tissue. For example under certain circumstances, benzoporphyrin derivative becomes present within the ciliary body within 5 minutes of administration.

Effective treatments in certain embodiments occur at times in the range of about one minute to about three hours following administration of the photosensitizer. However, as with green porphyrins, it is undesirable to perform the PDT within the first five minutes following administration to prevent undue damage to collateral blood vessels and tissues still containing relatively high concentrations of photosensitizer.

In certain embodiments of the invention, the treatment parameters are varied to reduce or eliminate evidence of corneal edema, corneal neovascularization, hyphema, and/or inflammation. For example, the size of the treatment area and/or the amount of the photosensitizer can be decreased.

The efficacy of PDT may be monitored using conventional methodologies for measuring intraocular pressure, including, for example, via applanation tonometry, non contact tonometry, contour tonometry, manometry, pneumotonometry and radiotelemetry.

In addition, the efficacy and selectivity of the PDT method may be enhanced by combining the PDT with an apoptosis-modulating factor administered prior to or concurrent with administration of the photosensitizer. An apoptosis-modulating factor can be any factor, for example, a protein (for example a growth factor or antibody), peptide, nucleic acid (for example, an antisense oligonucleotide, an aptamer, or a small interfering RNA), peptidyl nucleic acid (for example, an antisense molecule), organic molecule or inorganic molecule, that induces or represses apoptosis in a particular cell type. For example, it may be advantageous to prime the apoptotic machinery of cells in the ciliary body with an inducer of apoptosis prior to PDT so as to increase their sensitivity to PDT. Cells primed in this manner are contemplated to be more susceptible to PDT. This approach may also reduce the light dose (fluence) required to achieve a reduction in intraocular pressure and thereby decrease the level of damage on surrounding cells and tissues. Alternatively, the cells outside the ciliary body may be primed with an a repressor of apoptosis so as to decrease their sensitivity to PDT. In this approach, the PDT at a particular fluence can become more selective for the ciliary body.

Apoptosis involves the activation of a genetically determined cell suicide program that results in a morphologically distinct form of cell death characterized by cell shrinkage, nuclear condensation, DNA fragmentation, membrane reorganization and blebbing (Kerr et al. (1972) BR. J. CANCER 26: 239-257). At the core of this process lies a conserved set of proenzymes, called caspases, and two important members of this family are caspases 3 and 7 (Nicholson et al. (1997) TIBS 22:299-306). Monitoring their activity can be used to assess on-going apoptosis.

It has been suggested that apoptosis is associated with the generation of reactive oxygen species, and that the product of the $Bcl_{-2}$ gene protects cells against apoptosis by inhibiting the generation or the action of the reactive oxygen species (Hockenbery et al. (1993) CELL 75: 241-251, Kane et al. (1993) SCIENCE 262: 1274-1277, Veis et al. (1993) CELL 75: 229-240, Virgili et al. (1998) FREE RADICALS BIOL. MED. 24: 93-101). $Bcl_{-2}$ belongs to a growing family of apoptosis regulatory gene products, which may either be death antagonists ($Bcl_{-2}$, $Bcl-x_L$) or death agonists (Bax, Bak.) (Kroemer et al. (1997) NAT. MED. 3: 614-620). Control of cell death appears to be regulated by these interactions and by constitutive activities of the various family members (Hockenbery et al. (1993) CELL 75: 241-251). Several apoptotic pathways may coexist in mammalian cells that are preferentially activated in a stimulus-, stage-, context-specific and cell-type manner (Hakem et al. (1998) CELL 94: 339-352).

The apoptosis-inducing factor preferably is a protein or peptide capable of inducing apoptosis in cells, for example, the cells disposed in the ciliary body. One apoptosis inducing peptide comprises an amino sequence having, in an N- to C-terminal direction, KLAKLAKKLAKLAK (SEQ ID NO: 1). This peptide reportedly is non-toxic outside cells, but becomes toxic when internalized into targeted cells by disrupting mitochondrial membranes (Ellerby et al. (1999) NATURE MEDICINE 5:1032-1038). Other apoptosis-inducing factors include, for example, constatin (Kamphaus et al. (2000) J. BIOL. CHEM. 14: 1209-1215), tissue necrosis factor α (Lucas et al. (1998) BLOOD 92: 4730-4741) including bioactive fragments and analogs thereof, cycloheximide (O'Connor et al. (2000) AM. J. PATHOL. 156: 393-398), tunicamycin (Martinez et al. (2000) ADV. EXP. MED. BIOL. 476: 197-208), adenosine (Harrington et al. (2000) AM. J. PHYSIOL. LUNG CELL MOL. PHYSIOL. 279: 733-742). Furthermore, other apoptosis-inducing factors may include, for example, anti-sense nucleic acid or peptidyl nucleic acid sequences that reduce or turn off the expression of one or more of the death antagonists, for example ($Bcl_{-2}$, $Bcl-x_L$). Antisense nucleotides directed against $Bcl_{-2}$ have been shown to reduce the expression of $Bcl_{-2}$ protein in certain lines together with increased phototoxicity and susceptibility to apoptosis during PDT (Zhang et al. (1999) PHOTOCHEM. PHOTOBIOL. 69: 582-586). Furthermore, an 18 mer phosphorothiate oligonucleotide complementary to the first six codons of the $Bcl_{-2}$ open reading frame, and known as G3139, is being tested in humans as a treatment for non-Hodgkins' lymphoma.

Apoptosis-repressing factors include, survivin including bioactive fragments and analogs thereof (Papapetropoulos et al. (2000) J. BIOL. CHEM. 275: 9102-9105), CD39 (Goepfert et al. (2000) MOL. MED. 6: 591-603), BDNF (Caffe et al. (2001) INVEST. OPHTHALMOL. VIS. SCI. 42: 275-82), FGF2 (Bryckaert et al. (1999) ONCOGENE 18: 7584-7593), Caspase inhibitors (Ekert et al. (1999) CELL DEATH DIFFER 6: 1081-1068) and pigment epithelium-derived growth factor including bioactive fragments and analogs thereof. Furthermore, other apoptosis-repressing factors may include, for example, anti-sense nucleic acid or peptidyl nucleic acid sequences that reduce or turn off the expression of one or more of the death agonists, for example (Bax, Bak).

The type and amount of apoptosis-modulating factor to be administered may depend upon the PDT and cell type to be treated. It is contemplated, however, that optimal apoptosis-modulating factors, modes of administration and dosages may be determined empirically. The apoptosis modulating factor may be administered in a pharmaceutically acceptable carrier or vehicle so that administration does not otherwise adversely affect the recipient's electrolyte and/or volume balance. The carrier may comprise, for example, physiologic saline.

Protein, peptide or nucleic acid based apoptosis modulators can be administered at doses ranging, for example, from about 0.001 to about 500 mg/kg, more preferably from about 0.01 to about 250 mg/kg, and most preferably from about 0.1 to about 100 mg/kg. For example, nucleic acid-based apoptosis inducers, for example, G318, may be administered at doses ranging from about 1 to about 20 mg/kg daily. Furthermore, antibodies may be administered intravenously at doses ranging from about 0.1 to about 5 mg/kg once every two to four weeks. With regard to intravitreal administration, the apoptosis modulators, for example, antibodies, may be administered periodically as boluses a dosages ranging from about 10 μg to about 5 mg/eye and more preferably from about 100 μg to about 2 mg/eye.

The apoptosis-modulating factor preferably is administered to the mammal prior to PDT. Accordingly, it is preferable to administer the apoptosis-modulating factor prior to administration of the photosensitizer. The apoptosis-modulating factor, like the photosensitizer, may be administered in any one of a wide variety of ways, for example, orally, parenterally, or rectally. However, parenteral administration, such as intravenous, transscleral, intramuscular, subcutaneous, and intravitreal is preferred. Administration may be provided as a periodic bolus (for example, intravenously or intravitreally) or by continuous infusion from an internal reservoir (for example, bioerodable implant disposed at an intra- or extra-ocular location) or an external reservoir (for example, and intravenous bag). The apoptosis modulating factor may be administered locally, for example, by continuous release from a sustained release drug delivery device immobilized to an inner wall of the eye or via targeted transscleral controlled release into the choroid (see, PCT/US00/00207).

The invention is illustrated further by reference to the following non-limiting example.

EXAMPLE

Example 1 Ciliary Body Photodynamic Therapy Reduces Intraocular Pressure for a Prolonged Period of Time The purpose of this experiment is to demonstrate that benzoporphyrin derivative-based photodynamic therapy can reduce intraocular pressure (IOP) in eyes for a prolonged period of time.

This study employed liposomal benzoporphyrin derivative (verteporfin) as a photosensitizer, DBA/2J mice at least 8 months of age as the glaucoma model, and C57BL/6 mice as normal controls.

Briefly, verteporfin photosensitizer was injected intravenously at doses of 1.0 (DBA/2J), 2.0 (C57BL/6) or 4.0 (C57BL/6) mg/kg. Transscleral irradiation of the ciliary body was performed using light at a wavelength of 689 nm, delivered via an optical fiber, with irradiance of 1800 mW/cm$^2$ and fluence of 100 J/cm$^2$. One eye of each animal was treated and the fellow eye served as a control. The IOP was measured using an applanation tonometer with a fiber optic pressure sensor. The effect of PDT on structures was assessed by light and electron microscopy. Surviving retinal ganglion cells (RGC) in DBA/2J mice were retrogradely labeled with fluorogold 12 weeks after PDT. The mean IOP in treated eyes was significantly reduced compared to the control eyes in all groups. Significant reduction of mean IOP in DBA/2J mice lasted for 7 weeks, meanwhile the mean IOP in normal mice (2.0 and 4.0 mg/kg) returned to the level of the fellow control eyes by 7 and 17 days after treatment and retreatment, respectively. The mean numbers of RGC in DBA/2J treated eyes were significantly higher than control eyes.

(I) Materials and Methods
(a) Animal Model

All experiments were performed in accordance with the Association for Research in Vision and Ophthalmology Statement for the Use of Animals in Ophthalmic and Vision Research. C57BL/6 female mice aged 3 months (n=20) were used as the normal model. DBA/2J female mice aged 8 months (n=20) were used as the glaucoma mouse model. One eye of each animal was treated and the other eye served as a control (for both the normal and glaucoma models). Animals were housed in covered cages, were fed with a standard rodent diet ad libitum and were kept under constant 12 hour light-12 hour dark cycles. For general anesthesia, a mixture of ketamine (100 mg/kg) and xylazine (9 mg/kg) was administered intraperitoneally.

DBA/2J mice spontaneously develop essential iris atrophy, pigment dispersion, and glaucomatous changes. The IOP becomes elevated in most mice by the age of 9 months, which can be followed by ganglion cell loss, optic nerve atrophy and optic nerve cupping. As glaucoma developed, ganglion cell loss and mild cupping of the optic nerve were present in some animals by 11 months and in the majority of mice by the age of 22 months. The mean IOP of 6-month-old females typically are significantly higher than the mean IOP of males, and the IOP distributions of male and female mice shifted upward by 9 months.

(b) Photodynamic Therapy (PDT)

Verteporfin photosensitizer (Novartis Ophthalmics, Inc., Duluth, Ga.) was used in these experiments. The mice were systemically anesthetized prior to PDT, and the photosensitizer dye was administered to the animals by tail vain injections using a 30 G needle 5 minutes before laser irradiation. A dose of 2.0 or 4.0 mg/kg was used in C57BL/6 normal mice and of 1.0 mg/kg was used in DBA/2J mice. The laser irradiation to the ciliary body was applied transsclerally using a 600 μm optical fiber at a wavelength of light of 689 nm from a Diode Laser, with an irradiance of 1800 mW/cm$^2$ and a fluence of 100 J/cm$^2$ (Lumenis, Santa Clara, Calif.). Transscleral irradiation of the ciliary body was performed with applications for 360 degrees of the corneoscleral limbus in C57BL/6 normal mice and for 180 degrees in DBA/2J mice. In the C57BL/6 and DBA/2J mice, 16 and 8 spots, respectively, were irradiated to overlap with one another. In the eyes prepared for lectin labeling and terminal deoxynucleotide transferase-mediated nick end labeling (TUNEL) staining (a measure of apoptosis), PDT was performed in C57BL/6 mice to cover 180 degrees of the ciliary body at a 4.0 mg/kg verteporfin dose to compare the degree of staining between irradiated area and non-irradiated area. Retreatment was performed in C57BL/6 normal mice which had been treated with 2.0 mg/kg of verteporfin after the IOP measurement at post-PDT day 7 using the same light parameters.

This study used a relatively small dose of verteporfin and involved a relatively small area of irradiation for DBA/2J mice because when 2 mg/kg of verteporfin was preliminarily injected into DBA/2J mice and irradiated in 360 degrees of the corneoscleral limbus, severe damage such as corneal edema, hyphema, and corneal neovascularization occurred with high frequency. After the change of parameters, these complications were not seen.

Without wishing to be bound by theory, it is contemplated that the more pigment in the ciliary body of an eye, the more it may interfere with PDT. Pigment in the ciliary body may play a protective role against PDT, and the more pigmented C57BL/6 mice may be more resistant to treatment. Tsilimbaris et al. reported that the IOP reduction of pigmented rabbits by ciliary body PDT with CASPc lasted a relatively shorter period than that of albino rabbits. (Tsilimbaris et al. (1997) OPTHALMIC SURG LASERS 28: 483-94; Tsilimbaris et al. (2000) CURR EYE RES 20: 469-79). Since DBA/2J mice develop pigment dispersion, there may be a decrease in pigment in the ciliary body. Experimentally, the eyes of the DBA/2J mice readily transilluminated during treatment compared to the C57BL/6, a more pigmented eye. Also, by the age of 11 to 15 months, the ciliary processes in DBA/2J mice are usually fewer, shorter and narrower than those of young DBA/2J mice. As such, the ciliary body epithelium of DBA/2J mice at age 8-10 months old may have already started to decrease in size and number and may not be able to compensate for the injury induced by PDT.

(c) IOP Measurement

The IOP was measured using a previously reported applanation tonometer (Ahamed et al. (2003) IOVS 44:ARVO E-Abstract 3336) (n=12 in DBA/2J mice, n=5 in C57BL/6 mice at each dose). The principle of applanation tonometry employs fiber-optic gauges which are designed around a Fabry-Perot interferometer (FPI) (FTI-10; FISO Technologies, Inc., Quebec, Canada). FPI consists of two mirrors facing each other, the space separating the mirrors being called the cavity length. Light reflected in the FPI is wavelength-modulated in exact accordance with the cavity length. FPI gauges convert pressure into cavity length variations which correlate with IOP.

IOP was measured under general anesthesia. Standardization of the plane of anesthesia was obtained as described previously (John et al. (1997) INVEST. OPHTHALMOL. VIS. SCI. 38:249-53). Anesthesia was administered to one mouse at a time. After the mouse lost consciousness and failed to respond to touch, IOP was measured as soon as possible (typically within 2 to 3 minutes of loss of consciousness). Then anesthesia was injected in the next mouse.

As soon as the mice were anesthetized sufficiently, they were placed on a surgical platform. When the pressure sensor applanated a central area of mouse cornea under a dissecting microscope, the IOP (psi) was measured by the device 10 times automatically. The resulting pressures were converted into mmHg units by multiplying the obtained mean value by 51.7. The LOP was measured every 2 days in the first week, then twice a week until 4 weeks after PDT, and then once a week until 8 weeks after PDT.

(d) Histology

Eyes were enucleated at 6 hours (only DBA/2J), at 1 and 7 days after treatment, and at the end of IOP follow up (8 weeks after treatment)(n=2 in each group at each time point) and processed for light and transmission electron microscopic examination. The eyes were bisected behind the limbus, placed in modified Karnovsky's fixative at 4° C. overnight, and then transferred to 0.1 M cacodylate buffer at pH 7.4. Ciliary body specimens were observed by stereomicroscopy at 1 day after PDT for normal mice in the 4.0 mg/kg dose-treated group. Tissues were postfixed in aqueous 2% osmium tetroxide, stained en bloc with Uranyl Acetate, dehydrated in graded ethanols, and embedded in Epon. One-micrometer-thick sections were stained with 0.5% toluidine blue in borate buffer for light microscopy and examined using a photomicroscope (Leica Microsystems, Wetzlar, Germany). Thin sections were stained with aqueous uranyl acetate, and Sato's lead stain, and examined with a transmission electron microscope (CM 10; Phillips, Eindhoven, The Netherlands).

(e) Lectin Labeling of Vascular Endothelial Cells and TUNEL Staining

Lectin labeling of vascular endothelial cells and TUNEL staining (to examine apoptotic cells) was performed 1 day after PDT in C57BL16 normal mice (n=2). In DBA/2J mice, only TUNEL staining was performed. PDT was performed to cover 180 degrees of the ciliary body at a dose of 4.0 mg/kg (C57BL/6) and 1.0 mg/kg (DBA/2J) verteporfin to compare the degree of staining between irradiated area and non-irradiated area. Non-operated fellow eyes (n=2) were used as controls. After sufficient anesthesia, the animals were perfused with 8 mL phosphate buffered saline (PBS) administered via a catheter in the left ventricle. After PBS perfusion, fluorescein-isothiocyanate (FITC)-coupled Concanavalin A lectin (20 μg/mL in PBS, pH 7.4, 5 mg/kg BW)(Vector Labs, Burlingame, Calif.) was then perfused to stain vascular endothelial cells. Four percent paraformaldehyde in 0.1 PBS (pH 7.4) was perfused following PBS perfusion to remove residual unbound lectin. Enucleated eyes were fixed in 4% paraformaldehyde in 0.1 PBS overnight and were immersed in graded sucrose in 0.1 PBS. The samples were embedded in optimal cutting temperature (OCT) compound (Tissue-Tek, Tokyo, Japan), and sectioned vertically at 10-μm. TUNEL staining was performed according to the manufacturer's protocol (Fluorescein In Situ Apoptosis Detection Kit; CHEMICON International, Temecula, Calif.) to detect retinal cell death induced by PDT. Sections were counterstained with 1 μg/mL of DAPI (SIGMA-ALDRICH, St. Louis, Mo.).

(f) Retinal Ganglion Cell (RGC) Count in DBA/2J Mice

Four weeks after the end of IOP follow up, RGC was counted in DBA/2J mice (11 months old) as described previously (Levkovitch-Verbin et al. (2000) INVEST. OPHTHALMOL. VIS. SCI. 41:4169-74, Danias et al. (2003) INVEST. OPHTHALMOL. VIS. SCI. 44:5151-62) with slight modification (n=4). After the mice were anesthetized, the skin over the cranium was incised, and the scalp was exposed. Holes approximately 2 mm in diameter were drilled in the skull 4 mm posterior to the bregma, 1 mm lateral to the midline on both sides of the midline raphe. The neurotracer dye fluorochrome (Fluoro-gold, Englewood, Colo.) (4% solution in saline) was directly applied (1 μL, at a rate of 0.5 μL/min) at a depth of 2 mm from the brain surface using a Hamilton syringe (Hamilton, Reno, Nev.). Skull openings then were sealed with antibiotic ointment. The overlying skin was sutured and antibiotic ointment applied externally.

Seven days after the application of fluorochrome, the eyes were enucleated. The retinas were dissected, fixed in 4% paraformaldehyde (PFA), and flatmounted onto glass slides. Cell counting was performed as previously described (Nakazawa et al. (2002) INVEST. OPHTHALMOL. VIS. SCI. 43:3319-26) under a fluorescence microscope (Leica Microsystems, Wetzlar, Germany) using a UV filter set. RGC densities were determined by counting the tracer-labeled RGCs in 12 distinct areas of $9.0 \times 10^{-2}$ mm$^2$ each (three areas per retinal quadrant at 1/6, 3/6 and 5/6 of the retinal radius). The density of fluorochrome-labeled RGCs was defined as the average number of cells in the 12 fields. Cell counting was performed in a masked fashion.

(g) Statistical Analysis

All values are presented as mean±SD. Paired groups of two were compared by paired t-test. To compare three groups, data were compared by ANOVA, with post hoc comparisons tested using the Bonferroni procedure. Probabilities of $P<0.05$ were considered to be statistically significant.

(II) Results

Histological studies showed that ciliary body blood vessels in C57BL/6 normal mice were open in control eyes and that patent capillaries were surrounded by two layers of pigmented epithelium and non-pigmented epithelium. The basal plasma membrane of the pigmented epithelium had marked infolding, indicating that the cells were actively involved in ion transport. However, 1 day after PDT, the ciliary processes in normal mice treated with 2.0 mg/kg verteporfin were enlarged due to edema compared to the controls. Most ciliary body blood vessels in treated eyes appeared thrombosed and all capillaries were damaged.

Endothelial cells were damaged, and leukocytes and erythrocytes were seen leaking outside of the vessels. The basal infoldings were abnormally separated due to edema. Erythrocytes and fluid were noted outside the vessels. Basal processes of the pigment epithelium around the vessels were distended. Cell nuclei and mitochondria in both layers appeared unchanged.

The same findings were observed in normal mice with 4.0 mg/kg verteporfin 1 day after PDT. The significant morphological changes in the ciliary body of mice were vascular injury, thrombosis with vacuolization of endothelial cells, extravasculum of leukocyte and erythrocytes and severe edema. Ciliary processes appeared pale and swollen compared to the controls.

7 days after PDT, ciliary body vessels had recanalized in C57BL/6 normal mice at both the 2.0 mg/kg dose and the 4.0 mg/kg dose. The size of ciliary processes appeared normal compared to the controls. Cytoplasmic and nuclear morphology were normal at 7 days after PDT. All capillaries were normally organized. Layering and organization were normal. Basal processes of the pigmented epithelium were again abundant though they appeared more compacted. Cytoplasmic and nuclear morphology were normal. There were no significant morphological changes between 2.0 mg/kg and 4.0 mg/kg dye dose in C57BL/6 mice at 1 and 7 days after PDT.

In contrast, in the DBA/2J mice, most ciliary body blood vessels in the treated eyes were thrombosed (also known as "closed"), and creation of large spaces containing exudative material was seen in the epithelial layer at 6 hours after PDT. Electron microscopy showed that ciliary body vessels were thrombosed with erythrocytes and platelets. Endothelia of blood vessels were damaged, and erythrocytes and fluid were leaking from the vessels. The basal infoldings were abnormally separated due to edema. Most epithelial cells were edematous, and some epithelial cells were disrupted. Organelle dissolution and rupture of the plasma membrane were seen. One day after PDT, most ciliary body blood vessels were still thrombosed, and the ciliary epithelium and stroma were severely damaged and edematous. The endothelium of blood vessels was severely damaged and some had disappeared. Large intercellular spaces occupied by exudates were seen. Electron microscopy showed that basal infoldings were stretched and swollen with exudate. Epithelial edema and abnormal intercellular fluid were remarkable. At 7 days after PDT, the edema was decreasing in the epithelial layers. Some of ciliary body blood vessels were still thrombosed and some ciliary epithelia were still showing edematous swelling. Electron microscopic findings showed that the basal infoldings were still separated due to edema. Some ciliary blood vessels were recanalyzed and endothelia were normally organized. Possible regenerative epithelia were seen, while vacuolations were still seen in the epithelial layer. At 8 weeks after PDT, ciliary body blood vessels were recanalized, and edema had disappeared. Some ciliary processes were small and flattened. However, it was difficult to tell the difference between the PDT treated and the untreated ciliary bodies because even some of the untreated ciliary processes showed atrophic changes at this age.

Inspection of sections through the untreated and treated areas of ciliary body in the C57BL/6 normal mice 1 day after PDT with 4.0 mg/kg verteporfin revealed that vessels in the ciliary body and sclera in the untreated eyes were well stained by lectin (green fluorescence) and that no TUNEL positive cells (red fluorescence) (TUNEL positive cells bring apoptotic cells) were observable. In contrast, however, there were some TUNEL positive cells in the ciliary body and retina of the PDT treated eyes. The vessels in the ciliary body on the treated side showed little staining with lectin (green fluorescence) because of thrombosis. In DBA/2J mice eyes, only TUNEL staining was performed 1 day after PDT. Many TUNEL positive cells were seen in the ciliary process in both the treated and untreated sides of the treated eye and no TUNEL positive cells were seen in the non-treated eye. TUNEL positive cells in the untreated side of the treated eye were located only inside the ciliary process, which indicated that only weak laser light impinged on the untreated side in the treated eye.

In normal mouse eyes treated with the 2 mg/kg dose of verteporfin photosensitizer, the mean baseline IOP was 13.2±2.4 mmHg for the left eye and 13.6±2.1 mmHg for the right eye (FIG. 1). There was no significant difference between the baseline measurements of control and treated eyes. The mean IOP of treated eyes was significantly reduced at 1 and 3 days after treatment compared to the control eyes, by 35.1% ($p<0.05$) and 41.3% ($p<0.01$) respectively. The mean IOP in the 2.0 mg/kg-treated group returned to the level of the fellow control eyes by 7 days after treatment. However, retreatment at 7 days after the first PDT significantly reduced the IOP again. The mean IOP of treated eyes was 8.7±2.6 mmHg and 9.5±2.1 mmHg at 10 and 14 days after first PDT, respectively. The mean IOP returned to the level of the counterpart control eyes by 17 days after PDT. The mean IOP in treated eyes were statistically lower than the level of fellow control eyes at 28 and 42 days after PDT.

Figure 2:
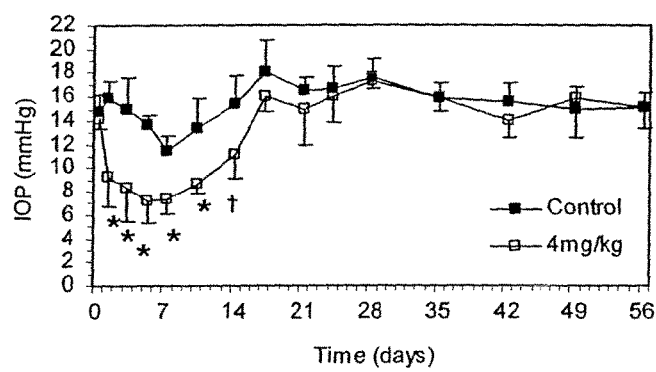
FIG. 2 is a graph showing the mean changes in intraocular pressure after PDT treatment of normal mice with 4.0 mg/kg verteporfin (open boxes) or without PDT treatment in a control eye (filled boxes). Values are mean±SD. *P<0.01 compared with controls. †P<0.05 compared with controls.

In normal mice treated with the 4 mg/kg dose of verteporfin photo sensitizer, the mean baseline IOP was 14.8±1.4 mmHg for the left eye and 14.2±0.9 mmHg for the right eye (FIG. 2). There was no significant difference between the baseline measurements of control and treated eyes. The mean IOP of treated eyes was significantly reduced (9.2±2.4 mmHg, $p<0.05$) at 1 day after treatment and reached a minimum (7.2±1.9 mmHg, $p<0.01$) at 5 days after treatment compared to the control eyes, by 42.1% and 47.3% respectively. Significant reduction of mean IOP lasted for 14 days and returned to the level of the fellow control eyes by 17 days after treatment.

Figure 3:
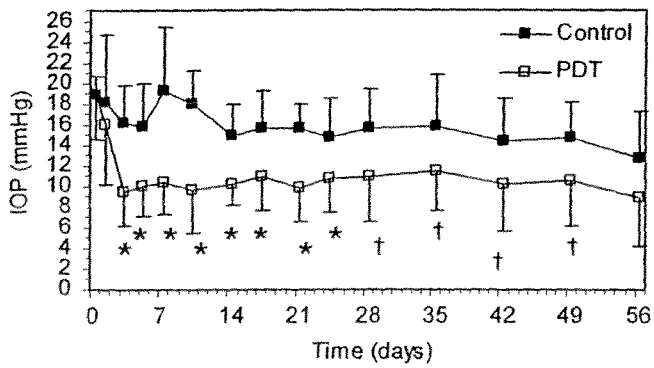
FIG. 3 is a graph showing the mean changes in intraocular pressure after PDT treatment of mice with glaucoma with 1.0 mg/kg verteporfin (open boxes) or without PDT treatment in a control eye (filled boxes). Values are mean±SD. *P<0.01 compared with controls. †P<0.05 compared with controls.

In DBA/2J glaucoma mice, the mean baseline IOP was 18.8±1.9 mmHg for the left eye and 18.8±4.3 mmHg for the right eye at 8 months of age (FIG. 3). The mean IOP 1 day after treatment was 18.2±6.5 mmHg and 15.9±5.7 mmHg in fellow control eyes and treated eyes, respectively. However, there was no significant difference between the two groups (i.e., the fellow control eyes and the treated eyes) 1 day after PDT. The mean IOP of treated eyes was significantly reduced by 40.8% compared to fellow control eyes 3 days after PDT (9.5±3.4 mmHg, $p<0.05$). Significant reduction of mean IOP lasted for at least 7 weeks notwithstanding the fact that intraocular pressure in both the control and treated eyes lowered over time. For example, in control fellow eyes, the mean IOP at 4 (9 months old) and 8 (10 months old) weeks after PDT were 15.6±3 7 mmHg and 12.6±4.7 mmHg, respectively. Although there was no significant difference between the mean IOP at 8 and 9 months of age, the mean IOP at 10 months was significantly lower than that at 8 months of age.

Figure 4:
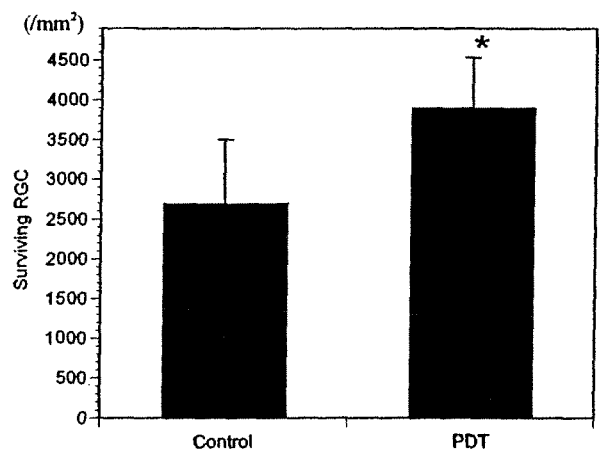
FIG. 4 is a bar chart showing retinal ganglion cell (RGC) survival at 11 months in animals having glaucoma. The values are mean±SD. P<0.05 compared with controls.

The number of retinal ganglion cells stained by fluorochrome in the eyes of DBA/2J control and treated eyes when the mice were 11 months of age is shown on FIG. 4. The number of retinal ganglion cells in the control eyes were 2701±798/mm$^2$ and the number of retinal ganglion cells in the treated eyes were 3905±627/mm$^2$. The loss of retinal ganglion cells over the 3 month period was significantly reduced in mice receiving PDT compared to DBA/2J controls (p<0.05).

The first chief histological finding after PDT of this study was thrombosis of the ciliary body vessels and tissue edema. Besides the light and electron microscopic findings, it has been found that the ciliary body vessels in treated eyes were not well stained by lectin 1 day after PDT, while vessels in untreated eyes were well stained. This result also indicates that the ciliary body vessels on the treated side were thrombosed and were not perfused by lectin 1 day after PDT.

In this study, ciliary body PDT significantly reduced the IOP in both animals. The strategy of ciliary body PDT is destruction of ciliary body epithelium which produces aqueous humor. Without wishing to be bound by theory, it is contemplated that oxygen radicals produced by ciliary body PDT may directly damage ciliary body epithelia and result in necrosis and/or apoptosis. Damaged vascular endothelium may lead to thrombosis and result in secondary injury. The experiments described herein show damage to the vascular endothelium in ciliary body morphologically, and that apoptotic cells were seen in the ciliary epithelium by TUNEL staining. These results indicate not only that transscleral PDT can induce ciliary body damage but also that apoptosis may be a mechanism by which PDT is effective in reduction of IOP. Electron microscopy after PDT in normal mouse eyes showed that basal processes of the pigment epithelium around the vessels were distended, but cell nuclei and mitochondria in both layers appear unchanged. The data suggest that transscleral ciliary body PDT may damage ciliary body more mildly than other cyclodestruction by cryotherapy or laser irradiation, and has potential for better control of IOP.

In DBA/2J mice, not only vascular thrombosis but also ciliary body epithelial injury was found during histological examination. In other words, effective IOP reduction was obtained with less laser power and less treated area. In light and electron microscopic findings, the ciliary body blood vessel occlusions were seen even on the untreated side in treated eyes. TUNEL staining also showed the untreated side had been irradiated and damaged to some extent. In preliminary experiments, 180° of the ciliary body was irradiated in normal mouse eyes using 2.0 mg/kg verteporfin, but significant IOP reduction was not obtained. In contrast, PDT using 1.0 mg/kg verteporfin with treatment of 180° resulted in a significant reduction of IOP in the DBA/2J mice. In this study, significant reduction of mean IOP lasted for at least 7 weeks in the PDT treated DBA/2J mice eyes, whereas significant reduction of mean IOP only lasted 7-17 days in treated normal mice eyes.

INCORPORATION BY REFERENCE

The entire disclosure of each of the patent and non-patent documents disclosed herein is expressly incorporated herein by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. A method of reducing intraocular pressure in a mammalian eye having a ciliary body for at least 4 weeks, the method comprising the steps of:
   (a) administering to a mammal, an amount of a benzoporphyrin derivative photosensitizer sufficient to accumulate in the ciliary body; and
   (b) within one minute to three hours following photosensitizer administration irradiating no more than 180 degrees of the ciliary body with light at a fluence of 50 Joules/cm$^2$ to 200 Joules/cm$^2$ so as to activate the benzoporphyrin derivative photosensitizer thereby to reduce intraocular pressure in the eye relative to intraocular pressure in the eye prior to irradiation for at least 4 weeks.

2. The method of claim 1, wherein the benzoporphyrin derivative photosensitizer is benzoporphyrin derivative mono-acid.

3. The method of claim 1, wherein the amount of the benzoporphyrin derivative photosensitizer is 1 mg/kg.

4. The method of claim 1, wherein the irradiating step comprises a fluence of 100 Joules/cm$^2$.

5. The method of claim 1, wherein the irradiating step comprises an irradiance of 1800 mW/cm$^2$.

6. The method of claim 1, wherein the fluence and irradiance conditions reduce the intraocular pressure in the eye by at least 20% of the intraocular pressure in the eye prior to irradiation.

7. A method of treating glaucoma in a mammalian eye having a ciliary body, the method comprising the steps of:

(a) administering to a mammal, an amount of a benzoporphyrin derivative photosensitizer sufficient to accumulate in the ciliary body; and (b) within one minute to three hours following photosensitizer administration irradiating no more than 180 degrees of the ciliary body with light at a fluence of 50 Joules/cm$^2$ to 200 Joules/cm$^2$ and an irradiance of 50 mW/cm$^2$ to 1800 mW/cm$^2$ so as to activate the benzoporphyrin derivative photosensitizer thereby to reduce intraocular pressure in the eye relative to intraocular pressure in the eye prior to irradiation for at least 4 weeks.

8. The method of claim 7, wherein the benzoporphyrin derivative photosensitizer is benzoporphyrin derivative mono-acid.

9. The method of claim 7, wherein the amount of the benzoporphyrin derivative photosensitizer is 1 mg/kg.

10. The method of claim 7, wherein the irradiating step comprises a fluence of 100 Joules/cm$^2$.

11. The method of claim 7, wherein the irradiating step comprises an irradiance of 1800 mW/cm$^2$.

12. The method of claim 7, wherein the fluence and irradiance conditions reduce the intraocular pressure in the eye by at least 20% of the intraocular pressure in the eye prior to irradiation.

13. A method of preserving retinal ganglion cell viability in a mammalian eye having a ciliary body and at risk of developing or having glaucoma, the method comprising the steps of:

(a) administering to a mammal, an amount of a benzoporphyrin derivative photosensitizer sufficient to accumulate in the ciliary body; and (b) within one minute to three hours following photosensitizer administration, irradiating no more than 180 degrees of the ciliary body with light at a fluence of 50 Joules/cm$^2$ to 200 Joules/cm$^2$ so as to activate the benzoporphyrin derivative photosensitizer thereby to preserve retinal ganglion cell viability and reduce intraocular pressure in the eye relative to intraocular pressure in the eye prior to irradiation for at least 4 weeks.

14. The method of claim 13, wherein the benzoporphyrin derivative photosensitizer is benzoporphyrin derivative mono-acid.

15. The method of claim 13, wherein the amount of the benzoporphyrin derivative photosensitizer is 1 mg/kg.

16. The method of claim 13, wherein the light comprises a wavelength of 689 nm.

17. The method of claim 13, wherein the irradiating step comprises a fluence of 100 Joules/cm$^2$.

18. The method of claim 13, wherein the irradiating step comprises an irradiance of 1800 mW/cm$^2$.

19. The method of claim 13, wherein the fluence condition reduces the intraocular pressure in the eye by at least 20% of the intraocular pressure in the eye prior to irradiation.

20. The method of claim 1, wherein the method reduces intraocular pressure in the eye relative to intraocular pressure in the eye prior to irradiation for at least 5 weeks, at least 6 weeks, at least 7 weeks, or at least 8 weeks.

21. The method of claim 7, wherein the method reduces intraocular pressure in the eye relative to intraocular pressure in the eye prior to irradiation for at least 5 weeks, at least 6 weeks, at least 7 weeks, or at least 8 weeks.

22. The method of claim 13, wherein the method reduces intraocular pressure in the eye relative to intraocular pressure in the eye prior to irradiation for at least 5 weeks, at least 6 weeks, at least 7 weeks, or at least 8 weeks.

23. The method of claim 1, wherein the method is cyclodestructive.

24. The method of claim 7, wherein the method is cyclodestructive.

25. The method of claim 13, wherein the method is cyclodestructive.

* * * * *

SEQUENCE LISTING

<160> NUMBER OF SEQ ID NOS: 1

<210> SEQ ID NO 1
<211> LENGTH: 14
<212> TYPE: PRT
<213> ORGANISM: Artificial
<220> FEATURE:
<223> OTHER INFORMATION: Apoptosis inducing peptide

<400> SEQUENCE: 1

Lys Leu Ala Lys Leu Ala Lys Lys Leu Ala Lys Leu Ala Lys
1               5                   10